US012779247B2

(12) United States Patent
Yamaguchi et al.

(10) Patent No.: US 12,779,247 B2
(45) Date of Patent: Nov. 3, 2026

(54) CHARGED PARTICLE BEAM IRRADIATION SYSTEM

(71) Applicant: SUMITOMO HEAVY INDUSTRIES, LTD., Tokyo (JP)

(72) Inventors: Takashi Yamaguchi, Kanagawa (JP); Shouhei Mizutani, Kanagawa (JP); Masayuki Araya, Nagano (JP); Yuya Sugama, Nagano (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 292 days.

(21) Appl. No.: 17/685,814

(22) Filed: Mar. 3, 2022

(65) Prior Publication Data

US 2022/0280811 A1 Sep. 8, 2022

(30) Foreign Application Priority Data

Mar. 3, 2021 (JP) ................................ 2021-033429

(51) Int. Cl.
*A61N 5/10* (2006.01)

(52) U.S. Cl.
CPC ......... *A61N 5/1043* (2013.01); *A61N 5/1048* (2013.01); *A61N 2005/1087* (2013.01); *A61N 2005/1095* (2013.01)

(58) Field of Classification Search
None
See application file for complete search history.

(56) References Cited

U.S. PATENT DOCUMENTS 6,814,694 B1 * 11/2004 Pedroni ................ A61N 5/1043 600/1
2005/0051740 A1 * 3/2005 Yanagisawa ........... A61B 90/96 250/492.1
2006/0226372 A1 10/2006 Yanagisawa et al.
2009/0242789 A1 10/2009 Tachikawa
2012/0316378 A1 12/2012 Torikai et al.
2014/0014851 A1 * 1/2014 Asaba .................. A61N 5/1043 250/396 R
2014/0094639 A1 4/2014 Zwart et al.
2015/0141732 A1 5/2015 Dessy et al.
2018/0161595 A1 * 6/2018 Fuentes ................ A61N 5/1049

(Continued)

FOREIGN PATENT DOCUMENTS

JP 2017-209372 A 11/2017

OTHER PUBLICATIONS

Extended Search Report issued in European Application No. 22159060.7, dated Jul. 14, 2022.

(Continued)

*Primary Examiner* — Eliza W Osenbaugh-Stewart
(74) *Attorney, Agent, or Firm* — Michael Best & Friedrich LLP

(57) ABSTRACT

A charged particle beam irradiation system irradiating an irradiation target in an object with a charged particle beam, includes a scanning electromagnet, an irradiator irradiating the irradiation target with the charged particle beam by performing scanning with the charged particle beam with the scanning electromagnet, an adjusting member adjusting a penumbra of the charged particle beam with the scanning performed, and a holder provided on the irradiator and holding the adjusting member.

5 Claims, 10 Drawing Sheets

(56) References Cited

U.S. PATENT DOCUMENTS

2019/0299029 A1* 10/2019 Inoue .................. A61N 5/1081

OTHER PUBLICATIONS

W.T. Chu et al., “Instrumentation for treatment of cancer using proton and light-ion beams”, Review of Scientiic Instruments, Submitted Jan. 14, 1993, Published online Jun. 4, 1998, pp. 2055-2122, vol. 64, Issue 8, DOI: 10.1063/1.1143946, American Institute of Physics.

Bernhard A. Ludewigh et al., “Accelerated helium-ion beams for radiotherapy and stereotactic radiosurgery”, Madical Physics, Jan.-Feb. 1991, vol. 18, No. 1, pp. 36-42, DOI: 10.1118/1.596696, American Association of Physicists in Medicine.

* cited by examiner

CHARGED PARTICLE BEAM IRRADIATION SYSTEM

RELATED APPLICATIONS

The content of Japanese Patent Application No. 2021-033429, on the basis of which priority benefits are claimed in an accompanying application data sheet, is in its entirety incorporated herein by reference.

BACKGROUND

Technical Field

Certain embodiments of the present invention relates to a charged particle beam irradiation system.

Description of Related Art

In the related art, a device is known as a charged particle beam irradiation system for performing treatment by irradiating a patient's affected part with a charged particle beam. In the charged particle beam irradiation system described in the related art, an irradiator performs the irradiation with the charged particle beam by a scanning method. In other words, the irradiator performs irradiation while moving the position of charged particle beam irradiation with respect to the affected part by scanning with a scanning electromagnet.

SUMMARY

According to an embodiment of the present invention, there is provided a charged particle beam irradiation system according to the present invention irradiating an irradiation target in an object with a charged particle beam and including: a scanning electromagnet; an irradiator irradiating the irradiation target with the charged particle beam by performing scanning with the charged particle beam with the scanning electromagnet; an adjusting member adjusting a penumbra of the charged particle beam with the scanning performed; and a holder provided on the irradiator and holding the adjusting member.

DETAILED DESCRIPTION

Figure 1:
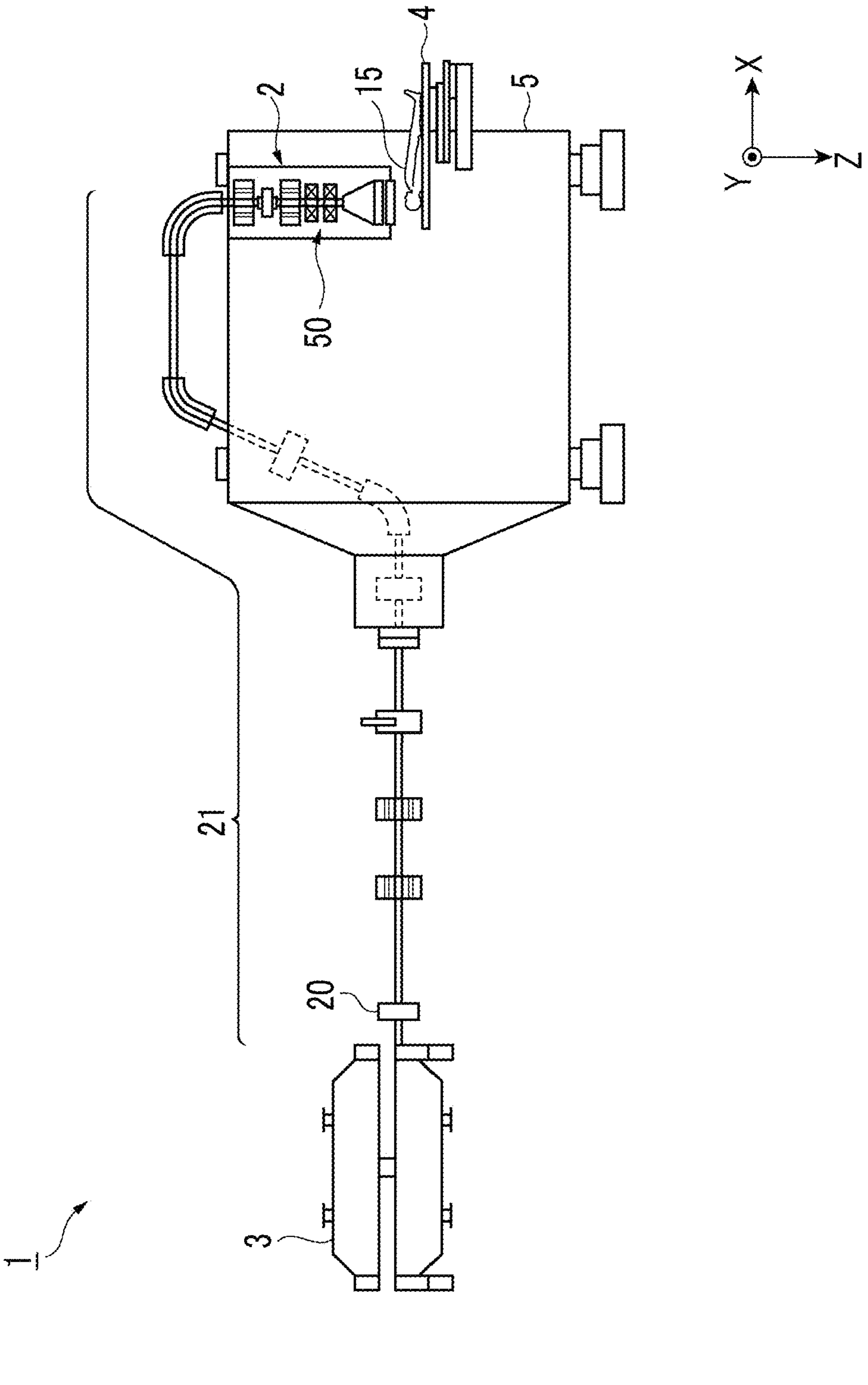
FIG. 1 is a schematic configuration diagram illustrating a charged particle beam irradiation system according to one embodiment of the present invention.

Ina case where the irradiator performs the irradiation with the charged particle beam by the scanning method, a treatment dose is applied to the outside of the irradiation target due to, for example, the large beam size of the charged particle beam. Accordingly, it has been required to appropriately irradiate an irradiation target with a charged particle beam.

The present invention is to provide a charged particle beam irradiation system capable of appropriately irradiating an irradiation target with a charged particle beam.

The charged particle beam irradiation system according to the present invention may include the irradiator irradiating the irradiation target with the charged particle beam by performing scanning with the charged particle beam with the scanning electromagnet and the adjusting member adjusting the penumbra of the charged particle beam. Accordingly, by the adjusting member adjusting the penumbra of the charged particle beam, it is possible to suppress the outside of the irradiation target being irradiated with the charged particle beam when the irradiator irradiates the vicinity of the boundary portion of the irradiation target. Here, the irradiator is provided with the holder holding the adjusting member. Accordingly, the irradiator is capable of irradiating the irradiation target with the charged particle beam in a state where the penumbra is adjusted at an appropriate position by the adjusting member. From the above, the irradiator is capable of appropriately irradiating the irradiation target with the charged particle beam.

The holder may be provided on a tip portion of the irradiator. In this case, the adjusting member is capable of adjusting the penumbra at a position close to the object. Accordingly, after the penumbra is adjusted by the adjusting member, the charged particle beam is quickly emitted to the irradiation target before an increase in beam spread.

The adjusting member may have a penumbra adjustment level in accordance with a depth of the irradiation target in the object. In this case, the adjusting member is capable of performing penumbra adjustment at a penumbra adjustment level in accordance with the depth of the irradiation target in the object.

In the charged particle beam irradiation system, a penumbra adjustment level of the adjusting member may be selectable based on a depth of the irradiation target in the object. In this case, the adjusting member is capable of performing penumbra adjustment at an appropriate penumbra adjustment level in accordance with the depth of the irradiation target in the object.

In the charged particle beam irradiation system, a penumbra adjustment level of the adjusting member may be selectable based on a distance between the object and the irradiator. In this case, the adjusting member is capable of performing penumbra adjustment at an appropriate penumbra adjustment level in accordance with the distance between the object and the irradiator.

The charged particle beam irradiation system may further include a detector detecting that the adjusting member that is erroneous is disposed with respect to the holder. In this case, it is possible to suppress the penumbra being adjusted by the adjusting member that is related to an inappropriate adjustment level.

Hereinafter, a charged particle beam irradiation system according to one embodiment of the present invention will be described with reference to the accompanying drawings. In the description of the drawings, the same elements are denoted by the same reference numerals with redundant description omitted.

FIG. 1 is a schematic configuration diagram illustrating a charged particle beam irradiation system 1 according to one embodiment of the present invention. The charged particle beam irradiation system 1 is used for radiation therapy-based cancer treatment or the like. The charged particle beam irradiation system 1 includes an accelerator 3 that accelerates charged particles generated by an ion source device and emits the particles as a charged particle beam, an irradiator 2 that irradiates an irradiation target with the charged particle beam, and a beam transport line 21 that transports the charged particle beam emitted from the accelerator 3 to the irradiator 2. The irradiator 2 is attached to a rotating gantry 5 provided so as to surround a treatment table 4. The irradiator 2 can be rotated around the treatment table 4 by the rotating gantry 5. More detailed configurations of the accelerator 3, the irradiator 2, and the beam transport line 21 will be described later.

Figure 2:
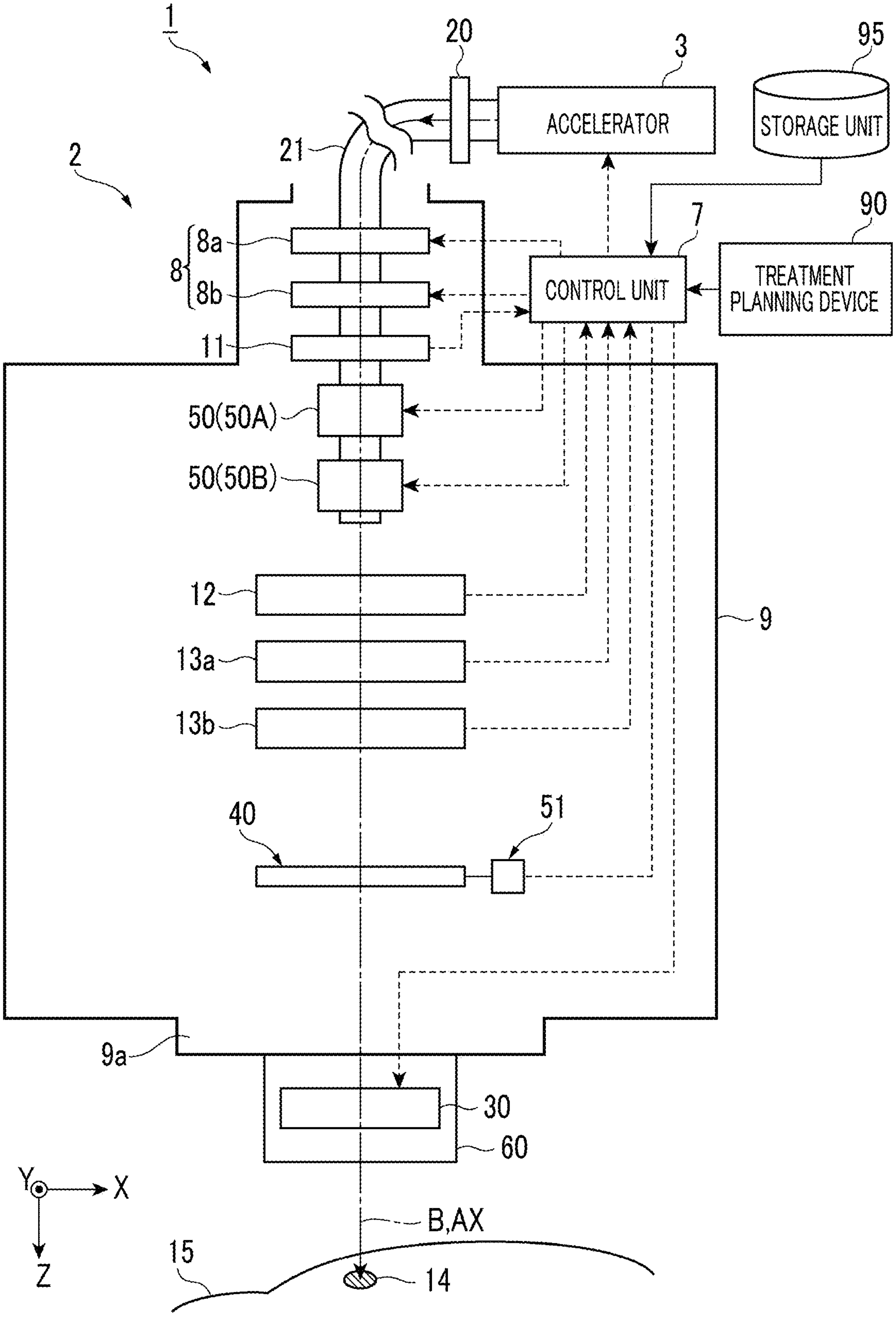
FIG. 2 is a schematic configuration diagram of the vicinity of an irradiator of the charged particle beam irradiation system of FIG. 1.

FIG. 2 is a schematic configuration diagram of the vicinity of the irradiator 2 of the charged particle beam irradiation system 1 of FIG. 1. "X-axis direction", "Y-axis direction", and "Z-axis direction" will be used in the following description. "Z-axis direction" is the direction in which a base axis AX of a charged particle beam B extends and is the depth direction of irradiation with the charged particle beam B. "Base axis AX" is the irradiation axis of the charged particle beam B that is not deflected by scanning electromagnets 50 (described later). FIG. 2 illustrates how irradiation with the charged particle beam B is performed along the base axis AX. "X-axis direction" is one direction in a plane perpendicular to the Z-axis direction. "Y-axis direction" is perpendicular to the X-axis direction in the plane perpendicular to the Z-axis direction.

First, a schematic configuration of the charged particle beam irradiation system 1 according to the present embodiment will be described with reference to FIG. 2. The charged particle beam irradiation system 1 is a scanning method-related irradiation device. The scanning method is not particularly limited, and line scanning, raster scanning, spot scanning, and so on may be adopted. As illustrated in FIG. 2, the charged particle beam irradiation system 1 includes the accelerator 3, the irradiator 2, the beam transport line 21, a control unit 7, a treatment planning device 90, and a storage unit 95.

The accelerator 3 is a device that accelerates charged particles and emits the charged particle beam B of preset energy. Examples of the accelerator 3 include a cyclotron, a synchrocyclotron, and a linac. In a case where a cyclotron that emits the charged particle beam B of predetermined energy is adopted as the accelerator 3, it is possible to adjust (decrease) the energy of the charged particle beam sent to the irradiator 2 by adopting an energy adjustment unit. The accelerator 3 is connected to the control unit 7, and a supplied current is controlled. The charged particle beam B generated by the accelerator 3 is transported to the irradiator 2 by the beam transport line 21. The beam transport line 21 connects the accelerator 3 and the irradiator 2 and transports the charged particle beam emitted from the accelerator 3 to the irradiator 2.

The beam transport line 21 has an energy regulator (energy selection system (ESS)) that adjusts the energy of the charged particle beam B during the transport. The beam transport line 21 has an energy degrader 20 near the outlet of the accelerator 3. The energy degrader 20 is a member that adjusts the range of the charged particle beam B and adjusts the depth of reach of the charged particle beam B in the body of a patient 15 (object). The energy degrader 20 adjusts the range by causing a loss in the energy of the charged particle beam B. The energy degrader 20 is capable of adjusting the range of the charged particle beam B by adjusting the thickness of a part through which the charged particle beam B passes. In addition to the energy loss at the energy degrader 20, the ESS also suppresses energy fluctuations and beam size expansion that occur in the beam transport line downstream of the ESS (using a collimator). The energy degrader 20 is made of a material such as beryllium and carbon. The energy degrader 20 is disposed at a position on the upstream side in the traveling direction of the charged particle beam B in the beam transport line 21 (that is, the accelerator 3 side). In the example illustrated in FIG. 1, the energy degrader 20 is disposed immediately behind the accelerator 3 in the path upstream of the rotating gantry 5, that is, on the most upstream side of the equipment (for example, electromagnet) of the beam transport line 21. However, the position of the energy degrader 20 in the beam transport line 21 is not particularly limited.

The irradiator 2 irradiates a tumor (irradiation target) 14 in the body of the patient 15 (object) with the charged particle beam B. The charged particle beam B is charged particles accelerated to a high speed, and examples thereof include a proton beam, a heavy particle (heavy ion) beam, and a particle beam. Specifically, the irradiator 2 is a device that irradiates the tumor 14 with the charged particle beam B emitted from the accelerator 3 accelerating the charged particles generated by the ion source (not illustrated) and transported by the beam transport line 21. The irradiator 2 includes the scanning electromagnets 50, a quadrupole electromagnet 8, a profile monitor 11, a dose monitor 12, position monitors 13*a* and 13*b*, a collimator 40, and a snout degrader 30 (adjusting member). The scanning electromagnets 50, the monitors 11, 12, 13*a*, and 13*b*, the quadrupole electromagnet 8, and the snout degrader 30 are accommodated in an irradiation nozzle 9 as an accommodating body. The irradiator 2 is configured by the irradiation nozzle 9 accommodating the main components as described above. The quadrupole electromagnet 8, the profile monitor 11, the dose monitor 12, and the position monitors 13*a* and 13*b* may be omitted.

An X-axis direction scanning electromagnet 50A and a Y-axis direction scanning electromagnet 50B are used as the scanning electromagnets 50. Each of the X-axis direction scanning electromagnet 50A and the Y-axis direction scanning electromagnet 50B is configured by a pair of electromagnets. The magnetic field between the pair of electromagnets is changed in accordance with the current supplied from the control unit 7, and scanning is performed with the charged particle beam B passing between the electromagnets. The X-axis direction scanning electromagnet 50A performs scanning with the charged particle beam B in the X-axis direction, and the Y-axis direction scanning electromagnet 50B performs scanning with the charged particle beam B in the Y-axis direction. The scanning electromagnets 50 are disposed in this order on the base axis AX downstream of the accelerator 3 in the traveling direction of the charged particle beam B. The scanning electromagnet 50 performs scanning with the charged particle beam B such that irradiation with the charged particle beam B is performed in a scan pattern pre-planned by the treatment planning device 90. How to control the scanning electromagnet 50 will be described later.

The quadrupole electromagnet 8 includes an X-axis direction quadrupole electromagnet 8*a* and a Y-axis direction quadrupole electromagnet 8*b*. The X-axis direction quadrupole electromagnet 8*a* and the Y-axis direction quadrupole electromagnet 8*b* throttle and converge the charged particle beam B in accordance with the current supplied from the control unit 7. The X-axis direction quadrupole electromagnet 8*a* converges the charged particle beam B in the X-axis direction, and the Y-axis direction quadrupole electromagnet 8*b* converges the charged particle beam B in the Y-axis direction. It is possible to change the beam size of the charged particle beam B by changing the throttle amount (convergence amount) by changing the current supplied to the quadrupole electromagnet 8. The quadrupole electromagnet 8 is disposed in this order on the base axis AX between the accelerator 3 and the scanning electromagnet 50. The beam size is the size of the charged particle beam B in the XY plane. The shape of the beam is the shape of the charged particle beam B in the XY plane.

The profile monitor 11 detects the beam shape and the position of the charged particle beam B for alignment at initial setting. The profile monitor 11 is disposed between the quadrupole electromagnet 8 and the scanning electromagnet 50 on the base axis AX. The dose monitor 12 detects the dose of the charged particle beam B. The dose monitor 12 is disposed downstream of the scanning electromagnet 50 on the base axis AX. The position monitors 13*a* and 13*b* detect and monitor the beam shape and the position of the charged particle beam B. The position monitors 13*a* and 13*b* are disposed on the base axis AX downstream of the dose monitor 12 in the traveling direction of the charged particle beam B. The monitors 11, 12, 13*a*, and 13*b* output detection results to the control unit 7.

The collimator 40 is provided at least downstream of the scanning electromagnet 50 in the traveling direction of the charged particle beam B. The collimator 40 is a member that blocks the charged particle beam B in part and allows the charged particle beam B to pass in part. Here, the collimator 40 is provided downstream of the position monitors 13*a* and 13*b*. The collimator 40 is connected to a collimator drive unit 51, which moves the collimator 40.

The snout degrader 30 reduces the energy of the charged particle beam B that passes to adjust the energy of the charged particle beam B. The snout degrader 30 is configured as an adjusting member adjusting the penumbra of the charged particle beam B. In the present embodiment, the snout degrader 30 is held by a holder 60 provided on a tip portion 9*a* of the irradiation nozzle 9. The tip portion 9*a* of the irradiation nozzle 9 is an end portion on the downstream side of the charged particle beam B. The snout degrader 30 and the holder 60 will be described in detail later.

The control unit 7 is configured by, for example, a CPU, a ROM, a RAM, and so on. The control unit 7 controls the accelerator 3, the thickness adjustment mechanism of the energy degrader 20, the scanning electromagnet 50, the quadrupole electromagnet 8, and the collimator drive unit 51 based on detection results output from the monitors 11, 12, 13*a*, and 13*b*.

In addition, the control unit 7 of the charged particle beam irradiation system 1 is connected to the treatment planning device 90 performing charged particle beam treatment planning and the storage unit 95 storing various data. The treatment planning device 90 measures the tumor 14 of the patient 15 by CT or the like before treatment and plans a radiation dose distribution at each position of the tumor 14 (radiation dose distribution of charged particle beams to be emitted). Specifically, the treatment planning device 90 creates a scan pattern with respect to the tumor 14. The treatment planning device 90 transmits the created scan pattern to the control unit 7. Planned in the scan pattern created by the treatment planning device 90 are a scanning path to be drawn by the charged particle beam B and the scanning speed at which the drawing is to be performed.

In a case where irradiation with the charged particle beam is performed by a scanning method, the tumor 14 is virtually divided into a plurality of layers in the Z-axis direction and scanning and irradiation with the charged particle beam are performed in one layer so as to follow the scanning path determined in the treatment planning. After the irradiation in the layer is completed, irradiation with the charged particle beam B is performed in the adjacent next layer.

In a case where irradiation with the charged particle beam B is performed by a scanning method and the charged particle beam irradiation system 1 illustrated in FIG. 2, the quadrupole electromagnet 8 is operated (ON) such that the passing charged particle beam B converges.

Subsequently, the charged particle beam B is emitted from the accelerator 3. Scanning with the emitted charged particle beam B is performed under the control of the scanning electromagnet 50 so as to follow the scan pattern determined in the treatment planning. As a result, the tumor 14 is irradiated with the charged particle beam B while being scanned within the irradiation range in one layer set in the Z-axis direction. The next layer is irradiated with the charged particle beam B after the irradiation in one layer is completed.

Figure 3A:
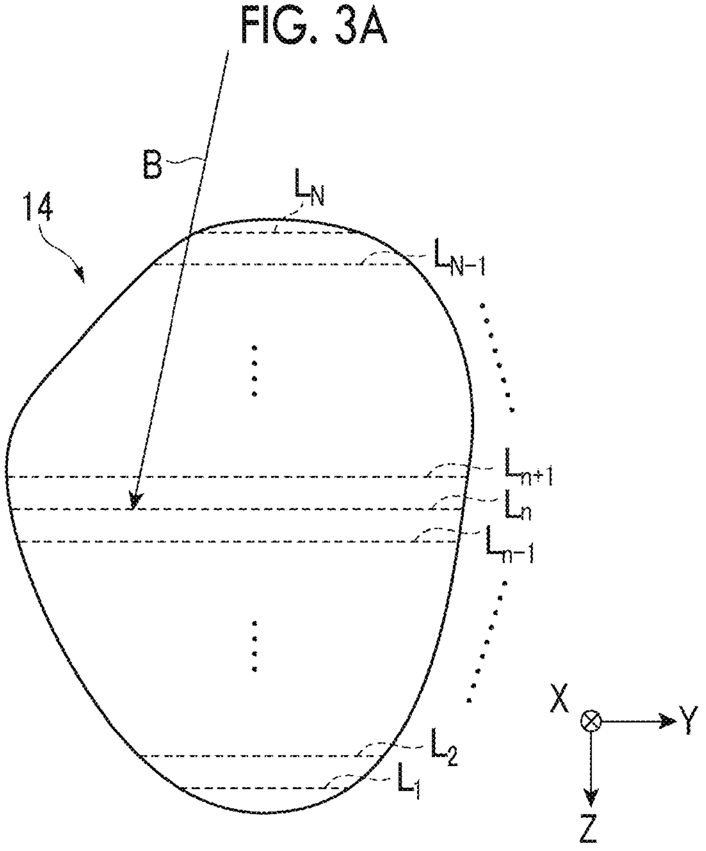
FIGS. 3A and 3B are diagrams illustrating layers set with respect to a tumor.
Figure 3B:
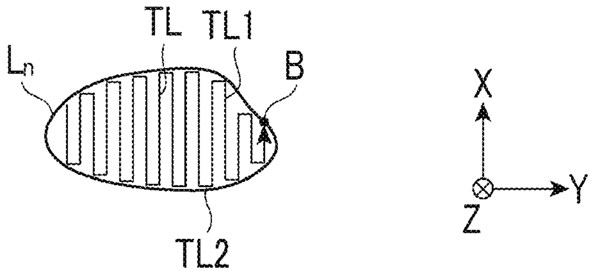

The charged particle beam irradiation image of the scanning electromagnet 50 controlled by the control unit 7 will be described with reference to FIGS. 3A and 3B. FIG. 3A illustrates an irradiation target virtually sliced into a plurality of layers in the depth direction. FIG. 3B illustrates a charged particle beam scanning image in one layer viewed from the depth direction.

As illustrated in FIG. 3A, the irradiation target is virtually sliced into a plurality of layers in the depth direction of irradiation and, in this example, is virtually sliced into the N layers of a layer L1, a layer L2, . . . a layer Ln−1, a layer Ln, a layer Ln+1, . . . a layer LN−1, and a layer LN in order from the deep layer (with a long range of the charged particle beam B). In addition, as illustrated in FIG. 3B, the charged particle beam B is, while drawing a beam trajectory along a scanning path TL, continuously emitted along the scanning path TL of the layer Ln in the case of continuous irradiation (line scanning or raster scanning) and emitted to a plurality of irradiation spots of the layer Ln in the case of spot scanning. The charged particle beam B is emitted along a scanning path TL1 extending in the X-axis direction, slightly shifted in the Y-axis direction along a scanning path TL2, and emitted along the adjacent scanning path TL1. In this manner, the charged particle beam B emitted from the irradiator 2 controlled by the control unit 7 moves on the scanning path TL.

Figure 4A:
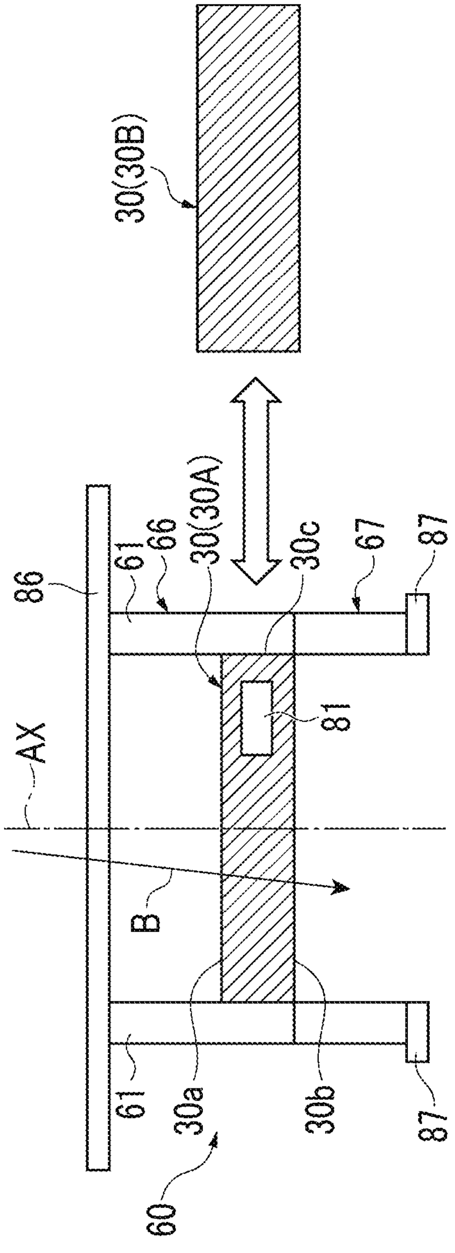
FIGS. 4A and 4B are schematic diagrams illustrating how a snout degrader is held by a holder.
Figure 4B:
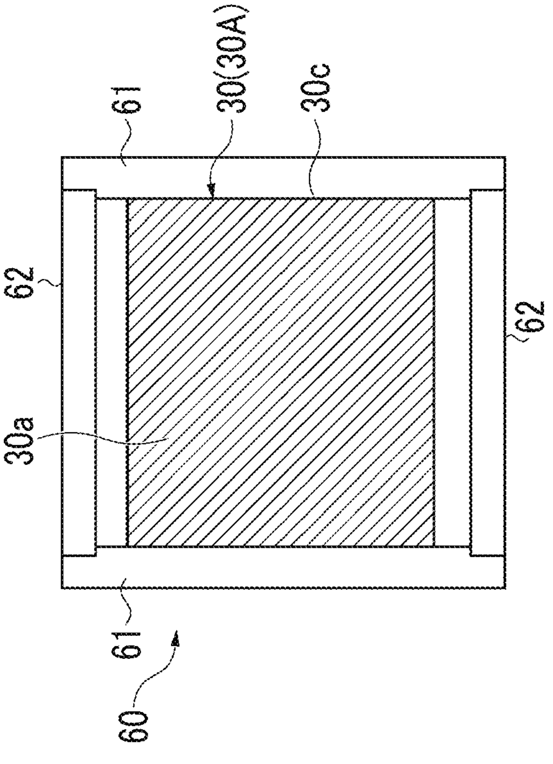

Next, the snout degrader 30 will be described in detail with reference to FIGS. 4 to 7. FIGS. 4A and 4B are schematic diagrams illustrating how the snout degrader 30 is held by the holder 60. As illustrated in FIGS. 4A and 4B, the snout degrader 30 is, for example, a member that has a rectangular plate shape. The snout degrader 30 has a planar incident surface 30*a* and a planar exit surface 30*b* extending in a direction perpendicular to the base axis AX. The snout degrader 30 has a uniform thickness in the range that is scanned with the charged particle beam B, and thus the snout degrader 30 attenuates constant energy. It is possible to change the energy adjustment amount of the charged particle beam B by changing the thickness of the snout degrader 30, that is, the dimension between the incident surface 30*a* and the exit surface 30*b*. As a result, the snout degrader 30 is capable of adjusting the penumbra of the charged particle beam B by adjusting the expansion of the beam size of the charged particle beam B. The snout degrader 30 is made of a material close in density to water, examples of which include polyethylene and acrylic. The snout degrader 30 is intended to adjust the spread of the charged particle beam B.

The irradiator 2 is provided with the holder 60 holding the snout degrader 30 on the irradiator 2 side. The holder 60 is provided on the tip portion 9*a* of the irradiation nozzle 9, and thus the snout degrader 30 is disposed downstream of every component in the irradiation nozzle 9, that is, at a position close to the patient 15. By being held by the holder 60, the snout degrader 30 is provided on the irradiator 2 side. The snout degrader 30 being provided on the irradiator 2 side is, for example, not a state where the snout degrader is disposed around the patient 15 or the snout degrader is attached to the bed of the patient 15 but a state where the snout degrader 30 is capable of moving as the irradiator 2 moves. The holder 60 is capable of holding the snout degrader 30 at a position closest to the patient 15 while holding the snout degrader 30 on the irradiator 2 side. At the position closest to the patient 15, the distance between the snout degrader 30 and the patient 15 is, for example, less than 30 cm. However, the distance between the snout degrader 30 and the patient 15 may be appropriately changed in relation to, for example, the surrounding environment.

The holder 60 has a pair of side wall portions 61 supporting outer peripheral edge portions 30*c* of the snout degrader 30. The holder 60 has a pair of side wall portions 62 facing the other outer peripheral edge portions 30*c* (see FIG. 4B). The side wall portions 61 and 62 extend downward from a support portion 86. Wide members 87 are provided in the tip portions of the side wall portions 61 and 62. In addition, the holder 60 is capable of holding the snout degraders 30 that are different in thickness. For example, the holder 60 is capable of holding a thick snout degrader 30B as well as a thin snout degrader 30A. In the case of a change in thickness, a user takes the thin snout degrader 30A out of the holder 60 and causes the holder 60 to hold the thick snout degrader 30B. Since the holder 60 is configured to be capable of holding the snout degraders that are different in thickness as described above, it can be said that the holder 60 has a configuration in which the level of penumbra adjustment, that is, thickness is selectable. The holder 60 may also serve as a bolus holder used in, for example, a wobbler irradiation method. Accordingly, the holder 60 may hold the snout degrader 30 with a bolus holder 66. In addition, the holder 60 may have a collimator holder 67 holding a collimator on the lower side of the bolus holder 66.

Figure 5:
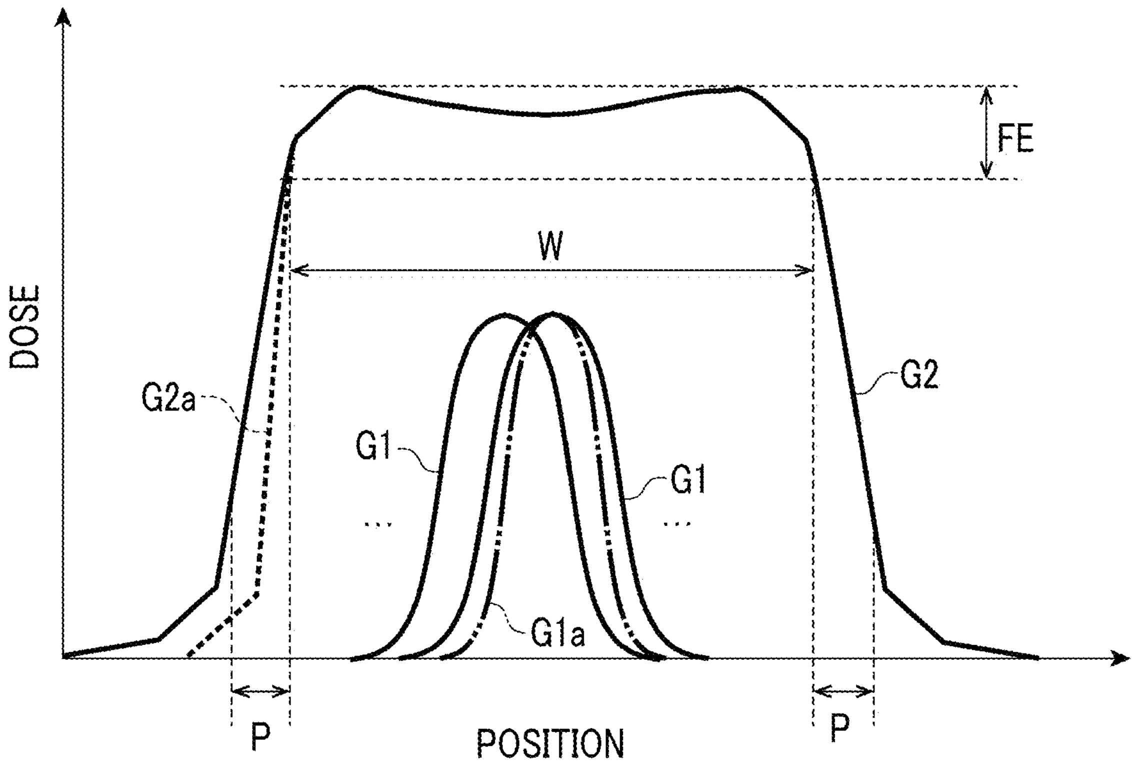
FIG. 5 is a graph illustrating the radiation dose distribution at a time when a charged particle beam is emitted by a scanning method into a predetermined plane perpendicular to a base axis.

Here, the penumbra will be described with reference to FIG. 5. FIG. 5 is a graph illustrating the radiation dose distribution at a time when the charged particle beam B is emitted by a scanning method into a predetermined plane perpendicular to the base axis AX. The horizontal axis indicates the position of the predetermined plane in a predetermined direction, and the vertical axis indicates the dose at each position. The graph in FIG. 5 is illustrated in a deformed manner for ease of understanding. Graph G1 in FIG. 5 illustrates the radiation dose distribution of the charged particle beam B per pass. As a result of scanning with the charged particle beam B in the predetermined plane, a plurality of slightly misaligned Graphs G1 are formed at the respective positions. Graph G2 illustrates the total radiation dose distribution that is obtained by overlapping these Graphs G1. The region indicated by W in FIG. 5 indicates a reference condition target width. The reference condition target width W indicates the width of the irradiation target in the plane. The width of the tumor 14 in the irradiation plane is the reference condition target width W. Graph G2 forms a flat region FE within the range of the reference condition target width W. The flat region FE is where the dose is substantially uniform and the difference in dose is within a predetermined range. The regions outside the reference condition target width W are penumbras P.

Here, the snout degrader 30 is capable of suppressing the expansion of the beam size of the charged particle beam B. Accordingly, in the case of penumbra suppression, the snout degrader 30 reduces the spread of the charged particle beam B (see Graph G1*a*). As a result, the radiation dose distribution changes as a whole, the spread of the charged particle beam B is also reduced, and thus the penumbra P can be suppressed (see Graph G2*a*).

Figure 6:
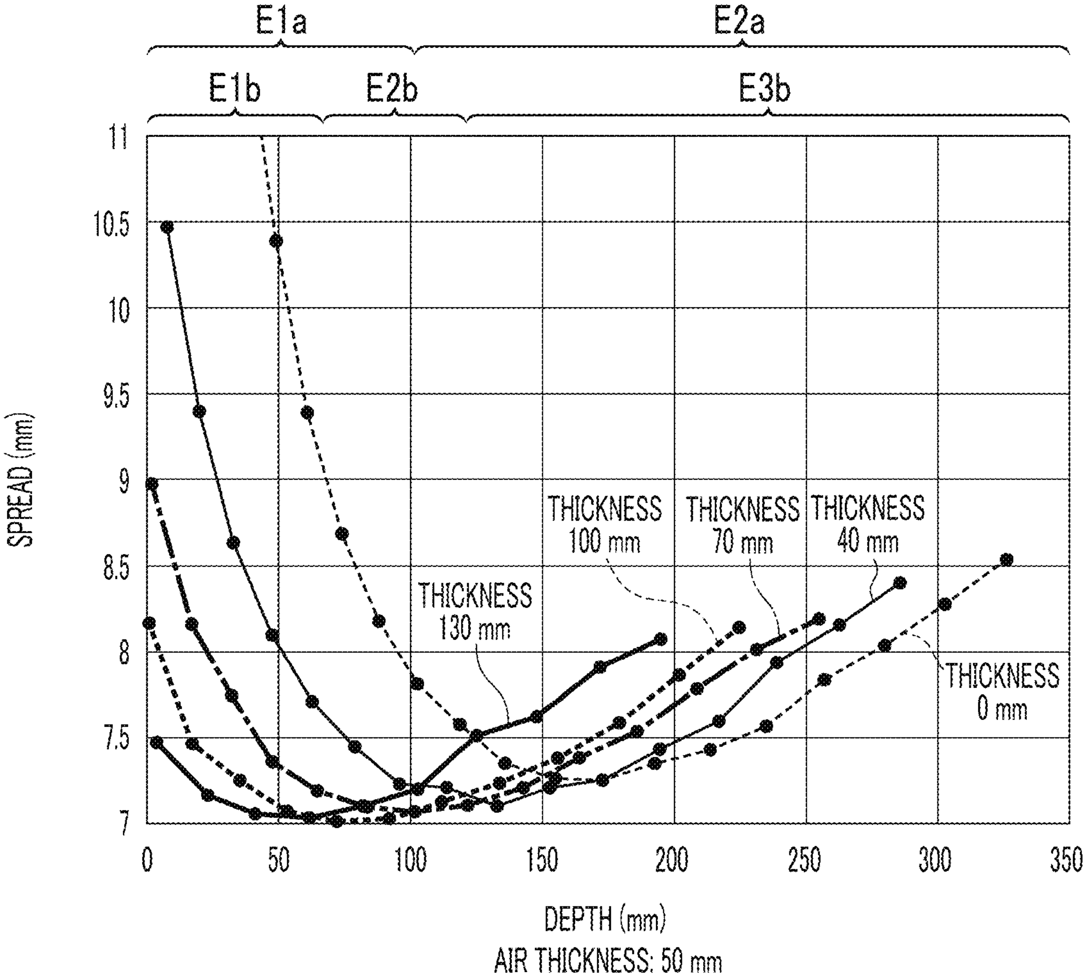
FIG. 6 is a graph illustrating a simulation result related to the relationship between the spread of the charged particle beam and the depth of an object.

FIG. 6 is a graph illustrating a simulation result related to the relationship between the spread of the charged particle beam B and the depth of an object. As for the graph in FIG. 6, the snout degrader 30 was set to certain thicknesses and the underwater spread of the charged particle beam B in the case of emission of the charged particle beam B into water was calculated at each thickness using Monte Carlo simulation. The horizontal axis indicates the distance from the surface of the water tank. This corresponds to the depth of the tumor 14 from the surface of the body of the patient 15. The vertical axis indicates the spread of the charged particle beam B. The spread is a value calculated by a method called Gaussian fitting. In FIG. 6, the distance between the snout degrader 30 and the water tank, that is, the thickness of the air layer through which the charged particle beam B emitted from the snout degrader 30 passes is set to 50 mm. This corresponds to the distance between the snout degrader 30 and the body surface of the patient 15.

As illustrated in FIG. 6, at a shallow part, the spread of the charged particle beam B can be suppressed more at a larger thickness of the snout degrader 30. At a deep part, the spread of the charged particle beam B can be suppressed more at a smaller thickness of the snout degrader 30. From such simulation results, the charged particle beam irradiation system 1 may be configured such that the penumbra adjustment level (here, thickness) of the snout degrader 30 can be selected based on the depth of the tumor 14 in the patient 15.

For example, the snout degrader 30 with a thickness of 13 cm may be selected in a case where the tumor 14 is at a shallow part Ela (less than 10 cm) in the body. The snout degrader 30 with a thickness of 0 cm or 4 cm may be selected in a case where the tumor 14 is at a deep part E2*a* (10 cm or more) in the body. The snout degrader 30 with a thickness of 12 cm may be selected in a case where the tumor 14 is at a shallow part E1*b* (less than 7 cm) in the body. The snout degrader 30 with a thickness of 8 cm may be selected in a case where the tumor 14 is at an intermediate part E2*b* (7 cm or more and less than 12 cm) in the body. The snout degrader 30 with a thickness of 0 cm or 4 cm may be selected in a case where the tumor 14 is at a deep part E3*b* (12 cm or more) in the body.

Figure 7:
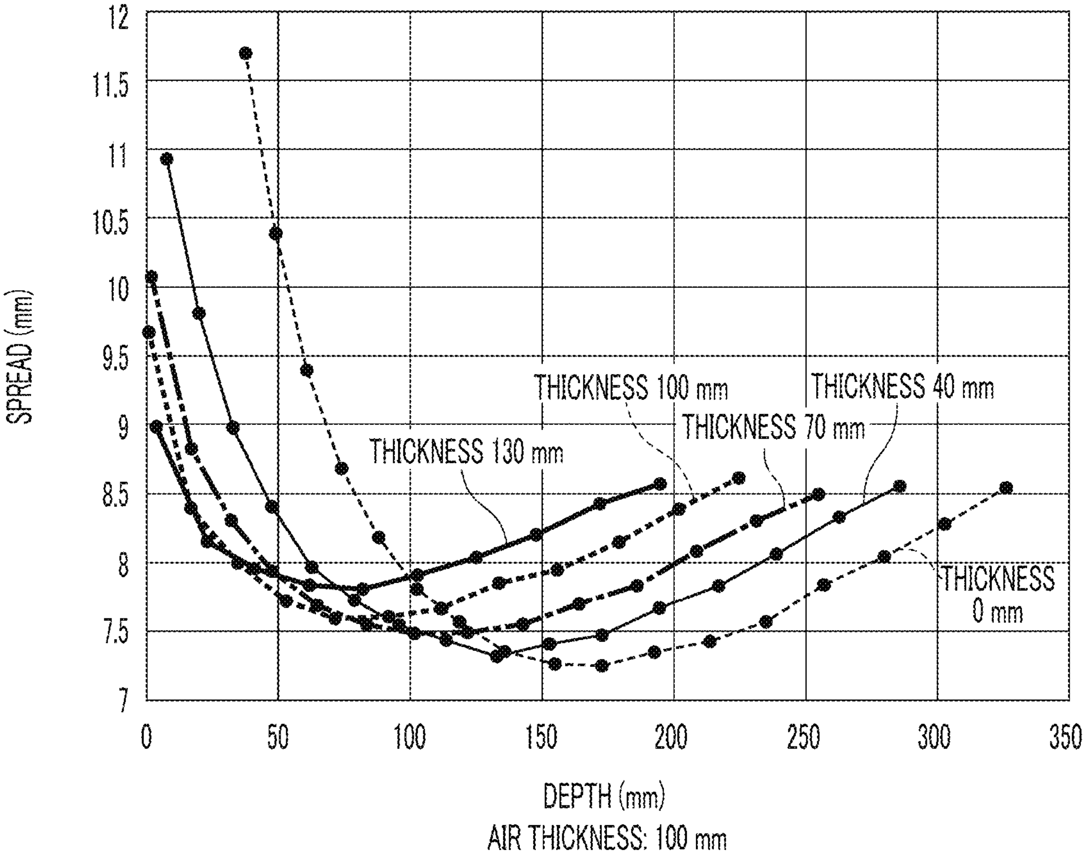
FIG. 7 is a graph illustrating a simulation result in which the thickness of an air layer is changed from FIG. 6.
Figure 8:
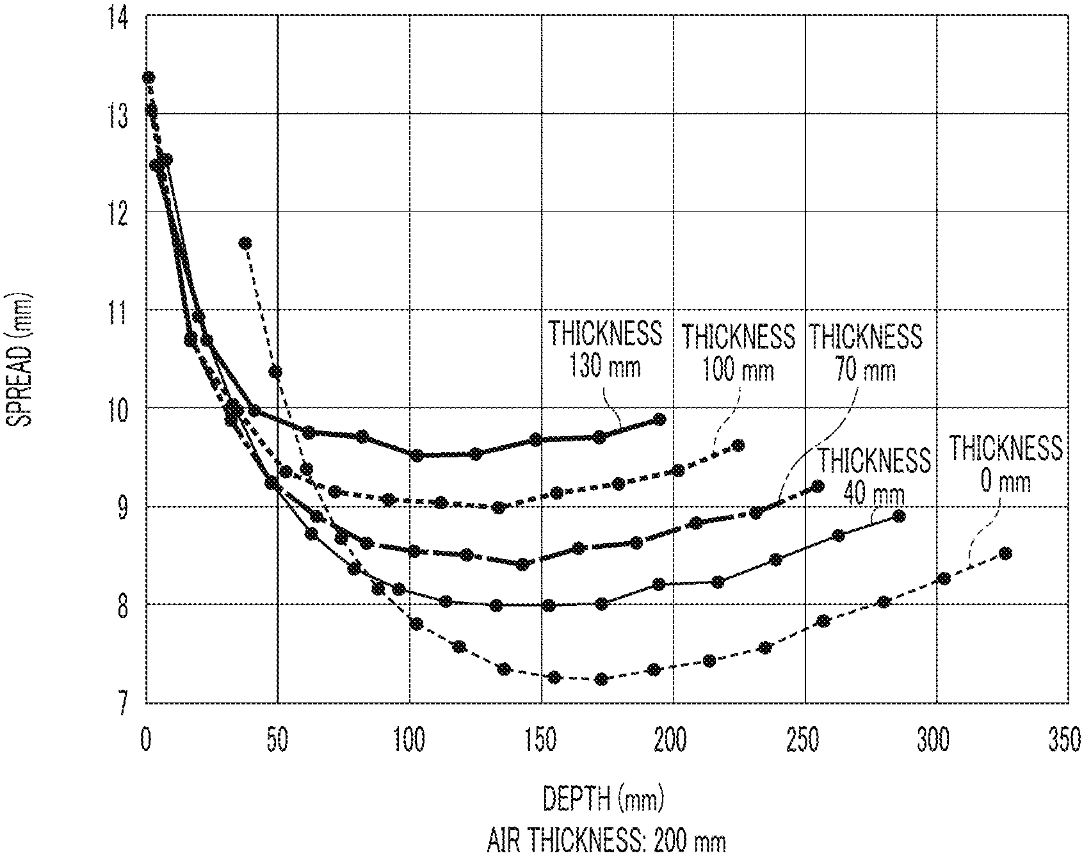
FIG. 8 is a graph illustrating a simulation result in which the thickness of the air layer is changed from FIG. 6.

FIGS. 7 and 8 are graphs illustrating simulation results in which the air layer thickness is changed from FIG. 6. The air layer thickness is 100 mm and 200 mm in the simulation results in FIGS. 7 and 8, respectively. As illustrated in FIGS.

6 to 8, the relationship between the depth of the snout degrader 30 of each thickness and the spread of the charged particle beam B changes depending on the air layer thickness. Accordingly, the charged particle beam irradiation system 1 may be configured such that the penumbra adjustment level (that is, thickness) of the snout degrader 30 can be selected based on the distance between the patient 15 and the irradiator 2 (see FIG. 2).

Figure 9:
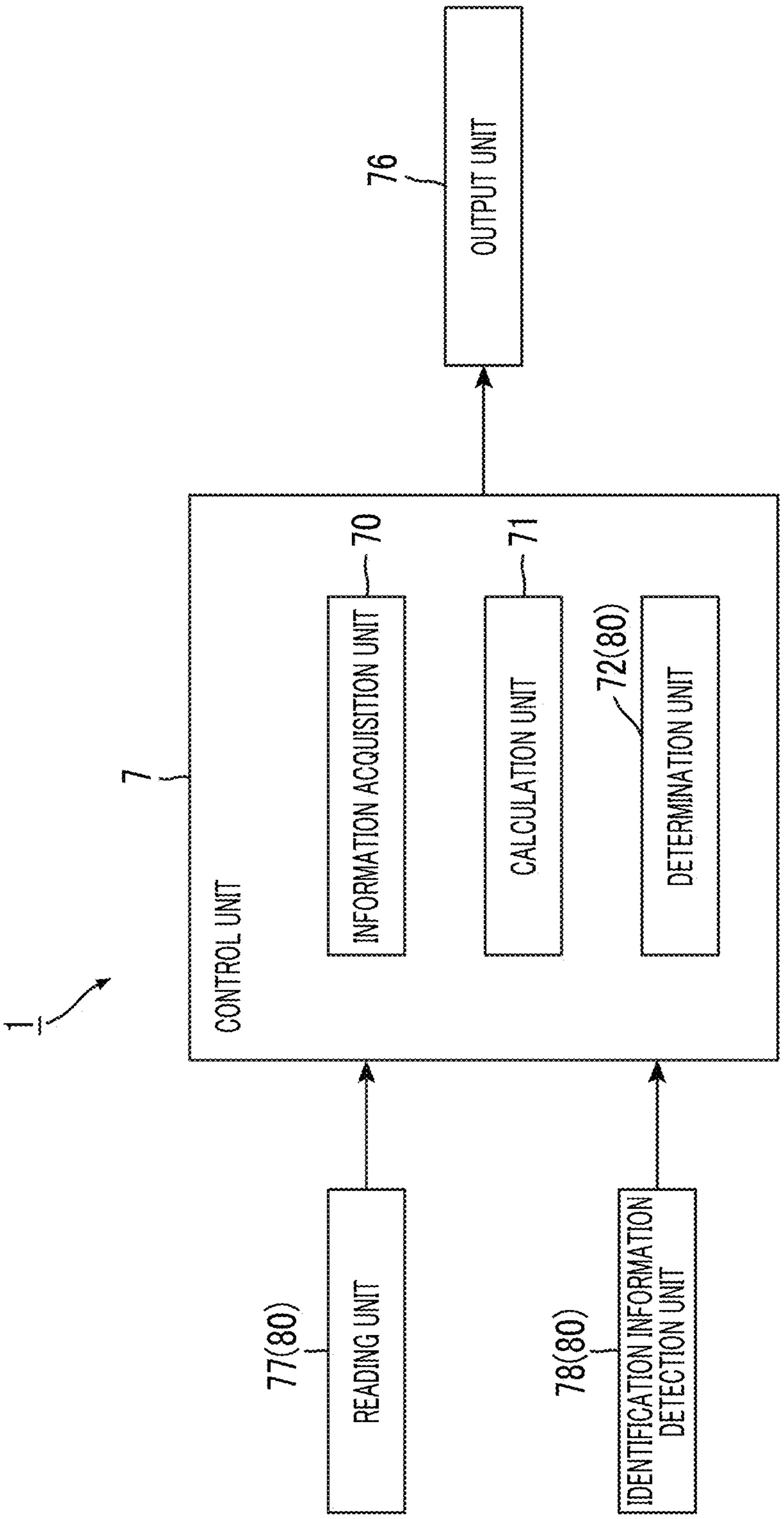
FIG. 9 is a block diagram illustrating a configuration for making the penumbra adjustment level of the snout degrader selectable.

Next, a configuration with which the penumbra adjustment level (that is, thickness) of the snout degrader 30 can be selected will be described with reference to FIGS. 4 and 9. FIG. 9 is a block diagram illustrating the configuration for making the penumbra adjustment level of the snout degrader 30 selectable. As illustrated in FIG. 9, the charged particle beam irradiation system 1 includes the control unit 7, an output unit 76, a reading unit 77, and an identification information detector 78. The control unit 7 includes an information acquisition unit 70, a calculation unit 71, and a determination unit 72.

The information acquisition unit 70 acquires various types of information related to irradiation with the charged particle beam B from the treatment planning device 90 and the storage unit 95. The information acquisition unit 70 is capable of acquiring information on the depth of the tumor 14 in the patient 15 and information on the distance between the patient 15 and the irradiator 2 (see FIG. 2) from the treatment planning created by the treatment planning device 90. The calculation unit 71 performs various types of calculation related to the selection of the penumbra adjustment level of the snout degrader 30. The calculation unit 71 selects the penumbra adjustment level, that is, thickness of the snout degrader 30 based on at least one of the information on the depth of the tumor 14 in the patient 15 and the information on the distance between the patient 15 and the irradiator 2 (see FIG. 2). The calculation unit 71 may select the thickness of the snout degrader 30 by, for example, collation between the acquired information and data pre-prepared as illustrated in FIGS. 6 to 8. Alternatively, the calculation unit 71 may select an appropriate thickness of the snout degrader 30 by performing calculation based on the acquired information. Alternatively, the appropriate thickness may be selected by the treatment planning device 90. In this case, the information acquisition unit 70 acquires information on the thickness of the snout degrader 30. The determination unit 72 determines whether or not the snout degrader 30 that is correct is disposed in the holder 60.

The output unit 76 outputs various types of information. The output unit 76 is configured by a monitor, a speaker, and so on. The output unit 76 may, for example, output information on the selected thickness of the snout degrader 30 to a user. As a result, the user can dispose the snout degrader 30 having the thickness selected by the control unit 7 in the holder 60.

Here, the reading unit 77, the identification information detector 78, and the determination unit 72 are configured as a detector 80 detecting that the snout degrader 30 that is erroneous is disposed with respect to the holder 60.

Specifically, the reading unit 77 reads thickness-related information from a thickness information holder 81 (see FIG. 4A) assigned with respect to each snout degrader 30. The thickness information holder 81 is not particularly limited insofar as the thickness information holder 81 is capable of holding thickness-related information and may be configured by, for example, a barcode. In this case, the reading unit 77 is configured by a barcode reader. In addition, the thickness information holder 81 may be configured by a QR code (registered trademark) with the reading unit 77 configured by a QR code reader. The thickness information holder 81 may be configured by means for holding magnetic information with the reading unit 77 configured by a device reading the magnetic information.

The identification information detector 78 detects information with which the snout degrader 30 held in the holder 60 can be identified. For example, the identification information detector 78 may detect a signal from predetermined detection means provided in the holder 60 as identification information. With the snout degrader 30 held by the holder 60, the detection means may transmit a signal indicating the thickness of the held snout degrader 30 to the identification information detector 78.

The determination unit 72 determines whether or not the thickness selected by the calculation unit 71 matches the thickness read by the reading unit 77. In a case where the thicknesses do not match, the determination unit 72 outputs information to the effect that the snout degrader 30 that is erroneous is disposed by the output unit 76. In a case where the thicknesses match, the determination unit 72 outputs information to the effect that the snout degrader 30 that is correct is disposed by the output unit 76.

The determination unit 72 performs comparison between the thickness information read by the reading unit 77 and the thickness selected by the calculation unit 71. In this case, a user can determine an error in advance by reading the thickness information with the reading unit 77 before the snout degrader 30 is disposed in the holder 60. In addition, the determination unit 72 identifies the thickness of the snout degrader 30 held by the holder 60 from the identification information detected by the identification information detector 78 and performs comparison between the thickness and the thickness selected by the calculation unit 71. In this case, the user can determine an error without performing a reading operation with the reading unit 77.

Figure 10:
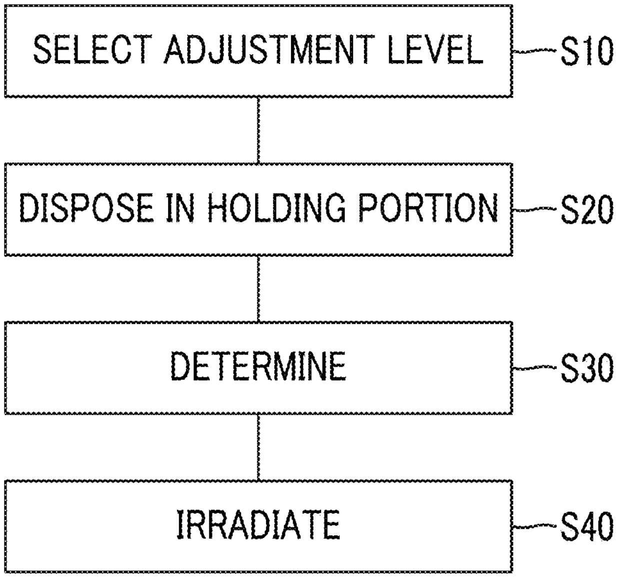
FIG. 10 is a process diagram illustrating the content of a charged particle beam irradiation method according to one embodiment of the present invention.

Next, a charged particle beam irradiation method according to the present embodiment will be described with reference to FIG. 10. FIG. 10 is a process diagram illustrating the content of the charged particle beam irradiation method according to the present embodiment. Executed as illustrated in FIG. 10 is Step S10 of selecting the penumbra adjustment level (that is, thickness) of the snout degrader 30 based on at least one of the depth of the tumor 14 in the body of the patient 15 and the distance between the patient 15 and the irradiator 2. Executed next is Step S20 of disposing the snout degrader 30 selected in Step S10 in the holder 60. Executed next is Step S30 of determining whether or not the snout degrader 30 that is erroneous is disposed in the holder 60 using the detector 80 (see FIG. 9). In a case where the reading unit 77 is used, Step S30 for the determination is executed prior to Step S20. Next, with the snout degrader 30 that is correctly disposed, Step S40 of the irradiator 2 emitting the charged particle beam B toward the tumor 14 is executed.

Next, the action and effect of the charged particle beam irradiation system 1 and the charged particle beam irradiation method according to the present embodiment will be described.

The charged particle beam irradiation system 1 according to the present embodiment includes the irradiator 2 irradiating the tumor 14 with the charged particle beam B by performing scanning with the charged particle beam B with the scanning electromagnet 50 and the snout degrader 30 adjusting the penumbra of the charged particle beam B. Accordingly, by the snout degrader 30 adjusting the penumbra of the charged particle beam B, it is possible to suppress the outside of the tumor 14 being irradiated with the charged particle beam B when the irradiator 2 irradiates the vicinity of the boundary portion of the tumor 14. Here, the irradiator 2 is provided with the holder 60 holding the snout degrader 30. Accordingly, alignment can be easily performed between the charged particle beam B with which the tumor 14 is irradiated and the snout degrader 30. Accordingly, the irradiator 2 is capable of irradiating the tumor 14 with the charged particle beam B in a state where the penumbra is adjusted at an appropriate position by the snout degrader 30. As an example, a worker is required to align the snout degrader while considering the positional relationship between the patient 15 and the irradiator 2 in a case where the snout degrader is provided on the bed side of the patient 15 and, in this case, it is difficult to perform the alignment because it becomes difficult to see the patient 15. On the other hand, in the present embodiment, the snout degrader 30 has only to be held by the holder 60, and thus the alignment is performed with ease. From the above, the irradiator 2 is capable of appropriately irradiating the tumor 14 with the charged particle beam B.

The holder 60 may be provided on the tip portion 9*a* of the irradiator 2. In this case, the snout degrader 30 is capable of adjusting the penumbra at a position close to the patient 15. Accordingly, after the penumbra is adjusted by the snout degrader 30, the charged particle beam B is quickly emitted to the tumor 14 before an increase in spread.

The charged particle beam irradiation system 1 may be configured such that the penumbra adjustment level of the snout degrader 30 can be selected based on the depth of the tumor 14 in the body of the patient 15. In this case, the snout degrader 30 is capable of adjusting the penumbra at an appropriate penumbra adjustment level in accordance with the depth of the tumor 14 in the body of the patient 15.

The charged particle beam irradiation system 1 may be configured such that the penumbra adjustment level of the snout degrader 30 can be selected based on the distance between the patient 15 and the irradiator 2. In this case, the snout degrader 30 is capable of adjusting the penumbra at an appropriate penumbra adjustment level in accordance with the distance between the patient 15 and the irradiator 2.

The charged particle beam irradiation system 1 may further include the detector 80 detecting that the snout degrader 30 that is erroneous is disposed with respect to the holder 60. In this case, it is possible to suppress the penumbra being adjusted by the snout degrader 30 that is related to an inappropriate adjustment level.

The charged particle beam irradiation method according to the present embodiment is a method for irradiating the tumor 14 in the body of the patient 15 with the charged particle beam B. The method includes Step S10 of selecting the penumbra adjustment level of the snout degrader 30 adjusting the penumbra of the charged particle beam B based on the depth of the tumor 14 in the body of the patient 15, Step S20 of disposing the snout degrader 30 that is selected with respect to the charged particle beam B, and Step S40 of irradiating the tumor 14 with the charged particle beam B by performing scanning with the charged particle beam B with the scanning electromagnet 50.

According to this charged particle beam irradiation method, the snout degrader 30 is capable of adjusting the penumbra at an appropriate penumbra adjustment level in accordance with the depth of the tumor 14 in the body of the patient 15. From the above, the tumor 14 can be appropriately irradiated with the charged particle beam B.

In treating a case in which a low-energy proton beam is generally used (for example, head and neck case) at a large hospital with a large number of patients, treatment using an adjusting member (snout degrader) as in the present embodiment leads to an improvement in the efficiency of beam use. The amount of proton beam use is limited in each facility, and thus high efficiency can lead to an increase in the number of treated patients as compared with existing ESS-based control.

The snout degrader 30 may have an adjustment level in accordance with the distance between the patient 15 and the irradiator 2. In this case, the snout degrader 30 is capable of adjusting the penumbra at the penumbra adjustment level that is in accordance with the distance between the patient 15 and the irradiator 2.

The charged particle beam irradiation method may further include Step S10 of selecting the adjustment level based on the depth of the tumor 14 in the body of the patient 15, and the snout degrader 30 that is selected may be disposed in Step S30 of disposing the snout degrader 30. In this case, the snout degrader 30 is capable of adjusting the penumbra at an appropriate penumbra adjustment level in accordance with the depth of the tumor 14 in the body of the patient 15.

The charged particle beam irradiation method may further include Step S10 of selecting the adjustment level based on the distance between the patient 15 and the irradiator 2, and the snout degrader 30 that is selected may be disposed in Step S30 of disposing the snout degrader 30. In this case, the snout degrader 30 is capable of adjusting the penumbra at an appropriate penumbra adjustment level in accordance with the distance between the patient 15 and the irradiator 2.

A charged particle beam irradiation system that does not have the snout degrader 30 on the tip portion 9*a* of the irradiator 2 will be described as, for example, a comparison example. In this case, the charged particle beam irradiation system controls the energy of the charged particle beam B with an energy regulator (energy selection system (ESS)) on the upstream side of the beam transport line 21. The energy regulator needs to cause a large energy loss at the energy degrader 20 so that the depth of reach of the charged particle beam B in a patient's body is changed. Accordingly, the charged particle beam B has a spread in the direction of movement. By the beam with the spread in the direction of movement being transported by the energy regulator, beam size and penumbra expansion results from drift as the charged particle beam B travels to the downstream side of the beam transport line 21.

On the other hand, in the charged particle beam irradiation system 1 according to the present embodiment, the snout degrader 30 adjusts the penumbra of the charged particle beam B directly in front of the patient 15. Accordingly, by keeping the energy loss at the energy degrader 20 on the upstream side small and increasing the energy loss for penumbra adjustment at the snout degrader 30, the patient 15 can be irradiated in a state where beam size expansion is suppressed and the penumbra can be suppressed. In addition, since the thickness of the snout degrader 30 is selectable, the penumbra adjustment level of the snout degrader 30 can be appropriately adjusted in accordance with the depth of the tumor 14 and the distance between the patient 15 and the irradiator 2.

The present invention is not limited to the embodiment described above.

For example, although the snout degrader has been exemplified as a penumbra adjusting member, another member may be adopted insofar as the member is capable of penumbra adjustment. For example, a collimator or a multi-leaf collimator may be provided at the position of the holder 60, that is, a position directly in front of the patient 15 and penumbra adjustment may be performed by the multi-leaf collimator. The multi-leaf collimator is capable of adjusting the penumbra by blocking the beam of the charged particle beam B at a position corresponding to the boundary portion of the tumor 14. The adjustment level can be adjusted by the opening diameter. The penumbra part is not blocked at a large opening diameter (that is, tumor outer diameter with a margin), and the penumbra can be blocked at a small opening diameter (fitted to the tumor outer diameter). In this case, it is possible to irradiate the tumor 14 with the charged particle beam B before an increase in the beam size of the charged particle beam B by adjusting the penumbra with the multi-leaf collimator in close proximity to the patient 15 (for example, 30 cm or less).

The position where a holder holding the multi-leaf collimator is provided does not necessarily have to be the tip portion of the irradiator. The holder may be provided in the irradiator.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation system irradiating an irradiation target in an object with a charged particle beam, the charged particle beam irradiation system comprising:

an accelerator configured to accelerate the charged particle beam and emit the charged particle beam;

a degrader configured to adjust a range of the charged particle beam and a depth of reach of the charged particle beam in the object;

an irradiator including a scanning electromagnet, an energy degrader, a holder, and a collimator and configured to irradiate the irradiation target with the charged particle beam by performing scanning with the charged particle beam with the scanning electromagnet; and a controller configured to select one of multiple thicknesses of the energy degrader, wherein the energy degrader is held by the holder and is configured to adjust a penumbra of the charged particle beam with the scanning performed, the collimator is provided between the scanning electromagnet and the energy degrader, the degrader is provided between the accelerator and the irradiator, the holder is configured to be able to hold multiple thicknesses of the energy degrader, and the controller is further configured to acquire a depth of the irradiation target in the object and information on a distance between the object and the irradiator, and to select a penumbra adjustment level by selecting, based on the acquired depth and information on the distance, one of the multiple thicknesses of the energy degrader according to pre-prepared data, the pre-prepared data quantitatively representing relationships among the distance, the penumbra adjustment level defined by a thickness of the energy degrader, and a spread of the charged particle beam.

2. The charged particle beam irradiation system according to claim 1, wherein the holder is provided on a tip portion of the irradiator.

3. The charged particle beam irradiation system according to claim 1, wherein the energy degrader has a penumbra adjustment level in accordance with a depth of the irradiation target in the object.

4. The charged particle beam irradiation system according to claim 3, wherein a penumbra adjustment level of the energy degrader is selectable based on a depth of the irradiation target in the object.

5. The charged particle beam irradiation system according to claim 1, wherein the controller is further configured to detect that the energy degrader that is erroneous is disposed with respect to the holder.

* * * * *